United States Patent [19]

Kobayashi et al.

[11] Patent Number: 5,039,868

[45] Date of Patent: Aug. 13, 1991

[54] METHOD OF AND APPARATUS FOR INSPECTING PRINTED CIRCUIT BOARDS AND THE LIKE

[75] Inventors: Shigeki Kobayashi, Shiga; Hideaki Takahara, Kyoto, both of Japan

[73] Assignee: Omron Corporation, Kyoto, Japan

[21] Appl. No.: 439,943

[22] Filed: Nov. 22, 1989

[30] Foreign Application Priority Data

Nov. 24, 1988 [JP] Japan .............................. 63-296928
Feb. 17, 1989 [JP] Japan .................................... 1-38993
Feb. 17, 1989 [JP] Japan .................................... 1-38994

[51] Int. Cl.⁵ ............................................. G01N 21/88
[52] U.S. Cl. ................................. 250/572; 356/376; 358/88
[58] Field of Search ............... 250/558, 572, 578.1; 382/8; 358/88; 356/12, 376, 237

[56] References Cited

U.S. PATENT DOCUMENTS

| | | | |
|---|---|---|---|
| 4,343,553 | 8/1982 | Nakagawa et al. | 356/376 |
| 4,541,007 | 9/1985 | Nagata | 358/88 |
| 4,571,616 | 2/1986 | Haisma et al. | 358/88 |
| 4,803,645 | 2/1989 | Ohtomo et al. | 356/376 |
| 4,894,790 | 1/1990 | Yotsuya et al. | 382/8 |
| 4,942,615 | 7/1990 | Sumi et al. | 356/376 |

FOREIGN PATENT DOCUMENTS 0231941 12/1987 European Pat. Off. .
8911093 11/1989 World Int. Prop. O. .

OTHER PUBLICATIONS

Patent Abstracts of Japan, vol. 10, No. 183 (P—472)(223), Jun. 26, 1986.
Patent Abstracts of Japan, vol. 11, 345 (P—636)(2792), Nov. 12, 1986.
Patent Abstracts of Japan, vol. 12, No. 90 (P—679)(2937), Mar. 24, 1988.
"A System for PCB Automated Inspection Using Fluorescent Light", I.E.E.E. Transactions On Pattern Analysis and Machine Intelligence, vol. 10, No. 1, Jan. 1988, pp. 69–78, New York, U.S.A.

*Primary Examiner*—David C. Nelms
*Assistant Examiner*—Stephone B. Allen
*Attorney, Agent, or Firm*—Fish & Richardson

[57] ABSTRACT

Disclosed is a substrate inspecting method in which light is projected to a part (21) mounted on a substrate (20) from a ring-shaped light source (29), reflected light form the surface of a soldered portion (44) is imaged by an imaging unit (32) and the nature of the soldered portion is inspected by its imaged pattern, characterized by applying fluorescent agents (70) to at least the periphery of the soldered portion of the mounted part on the surface of the substrate, exposing the surface coated with the fluorescent agents to light from the ring-shaped light source to excite the fluorescent agents, exposing the surface of the soldered portion to secondary illuminating light produced by the fluorescent agents to image its reflected light.

19 Claims, 15 Drawing Sheets

Fig. 7
| | SOLDERING IS ACCEPTABLE | PARTS ARE MISSING | SOLDER IS INSUFFICIENT IN QUANTITY |
|---|---|---|---|
| CROSS SECTION |  |  | 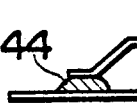 |
| IMAGED PATTERN |  | 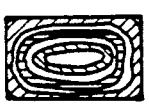 | 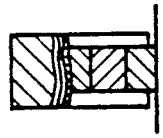 |
| RED PATTERN |  |  |  |
| GREEN PATTERN |  |  |  |
| BLUE PATTERN |  | 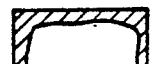 |  |

METHOD OF AND APPARATUS FOR INSPECTING PRINTED CIRCUIT BOARDS AND THE LIKE

BACKGROUND OF THE INVENTION

1. Field of the Invention

The present invention relates to methods of and apparatuses for inspecting printed circuit boards or substrates (referred to as substrates in this specification) used for inspecting parts mounted on the substrate for acceptability of soldering.

2. Description of the Related Art

Parts mounted on the surface of a substrate have been heretofore visually inspected for acceptability of their mounted state. In particular, the presence or absence, the amount, the solubility, the short, the inferior conduction, and the like of solder are visually inspected, to determine whether or not their soldered state is good. In such visual inspection, however, occurrence of inspection errors is not avoided, the results of the determination vary depending on inspectors, and there is a limitation to the inspection processing capability.

In recent years, various automatic inspecting apparatuses capable of automatically making this type of inspection have been proposed.

The surface of a soldered portion has a shape which extends in three dimensions. In order to inspect the shape, it is essential that information on three-dimensional shapes can be detected.

FIG. 1 shows an example of an automatic inspecting apparatus capable of inspecting information on three-dimensional shapes, which projects slit light 1 to a soldered portion on a substrate 2. Reflected light of a light cutting line 3 formed on the surface of the substrate 2 including the soldered portion by projecting the slit light 1 is imaged by an imaging unit 4. Its imaged pattern is examined, thereby to detect the three-dimensional shape of the soldered portion.

In this inspecting method, however, information on the shape of a portion illuminated by the slit light 1 is only obtained. Accordingly, it is difficult to grasp the three-dimensional shapes of other portions.

In order to solve this problem, there is provided a method of projecting light to the surface of a solid bounded by curved surface which is an object to be inspected from a plurality of directions at different angles of incidence, imaging its respective reflected light from the surface of the solid bounded by curved surface, and detecting the orientation of the element constituting the curved surface of the solid bounded by curved surface from their respective imaged patterns. This method belongs to an "active sensing method" which is one of methods of detecting information on three-dimensional images. More specifically, this method pays attention to the fact that, when a light beam having a constant pattern is projected to an object to be inspected, the pattern of its reflected light beam obtained from the object to be inspected is deformed corresponding to the three-dimensional shape of the object to be inspected, to estimate the shape of the object to be inspected from the deformed pattern.

FIG. 2 is a diagram for explaining the principle of this method, showing the positional relation between a detecting system comprising a light projecting unit 5 and an imaging unit 6 and a solid bounded by curved surface which is an object to be inspected.

It is assumed that, when a light beam 8 is projected to the surface of a solid bounded by curved surface for example, a soldered portion) 7 from the light projecting unit 5 arranged in a given position, its reflected light beam 9 is incident on the imaging unit 6 placed directly over the solid 7, to be detected. In this case, it is determined that the element of the curved surface of a portion illuminated by the light beam 8 to the solid bounded by curved surface 7 is oriented at an angle of $\theta$ with a horizontal reference surface 10 ($\theta$ is the angle of incidence). Accordingly, in a case where the nature of the surface of the solid bounded by curved surface 7 comprises a lot of elements of the curved surface oriented in different directions like the surface of the soldered portion, if light is projected to the surface of the solid 7 using a plurality of light projecting units having different angles of incidence, a group of elements of the curved surface corresponding to the respective angles of incidence is detected by the imaging unit 6. Consequently, it can be determined how each of the elements of the curved surface of the solid bounded by curved surface 7 is oriented, that is, how the nature of the surface of the soldered portion is.

Furthermore, if the light projecting unit 5 projects the light beam 8 having a width of $\Delta\theta$, the reflected light beam 9 having a width corresponding to the width is detected by the imaging unit 6. More specifically, in this case, the element of the curved surface having an angle of $\Delta\theta$ can be detected.

Additionally, if the light projecting unit 5 includes ring-shaped light sources 11, 12, 13 located horizontally relative to the reference surface 10, the distance between the light projecting unit 5 and the solid bounded by curved surface 7 is constant even if the solid 7 has any angle of rotation with an axis perpendicular to the reference surface 10. Accordingly, the orientation in the direction of the angle of rotation of the element of the curved surface is canceled. Consequently, only the angle of inclination of the solid bounded by curved surface 7 to the reference surface 10 is detected.

Furthermore, as shown in FIG. 3, if the light projecting unit 5 comprises a plurality of ring-shaped light sources 11, 12 and 13 having different angles of incidence to the solid bounded by curved body 7, the elements of the curved surface having orientations corresponding to the angles of incidence of light beams 14, 15 and 16 from the sources 11, 12 and 1 can be specifically detected as described above.

The three ring-shaped light sources 11, 12 and 13 having radii of $r_m$ (m=1, 2, 3) are horizontally arranged in positions at the heights $r_m$ (m=1, 2, 3) from a reference surface 10. In addition, let $\theta_m$ (m=1, 2, 3) be the angles of incidence of the light beams 14, 15 and 16 from the light sources 11, 12 and 13 to the solid bounded by curved surface 7. In this case, the elements of the curved surface respectively having angles of inclination of $\theta_m$ in the solid bounded by curved surface 7 can be detected by the imaging unit 6. The size of the element of the curved surface is sufficiently smaller than the total optical path length leading to the imaging unit 6 from the light sources 11, 12 and 13 through the surface of the solid bounded by curved surface 7. Consequently, the angle of incidence, that is, the angle of inclination of the element of the curved surface to be detected can be set by the following equation:

$$\cos\theta_m = h_m/(h_m^2 + r_m^2)^{\frac{1}{2}} \tag{1}$$

As a method of checking the appearance of a soldered portion on the basis of the above described principle, a method using white light sources as the light sources 11, 12 and 13 has been proposed (Japanese Patent Application laid-open Publication No. 61-293657). In this checking method, the three light sources 11, 12 and 13 having different angles of incidence to a soldered surface are respectively turned on or off at different timings so as to mutually identify images formed by reflected light from the light sources 11, 12 and 13.

However, in such a lighting control method, a memory for storing images obtained at different timings of projecting light, an arithmetic unit for executing an arithmetic operation taking the images as the same field image, a lightning unit for causing each of the light sources to instantaneously perform a lightning operation, and the like are required. Accordingly, the method is complicated from the technical standpoint, which presents problems in terms of the cost and the reliability.

In order to solve the problems in such a time sharing method once and for all, the applicant has proposed the following substrate inspecting apparatus (see Japanese Patent Application No. 63-112054).

This substrate inspecting apparatus is characterized by comprising light projecting means including three types of ring-shaped light sources for respectively producing such red, green and blue light, each having a light energy distribution using the wavelength to enter the horizontal axis, as to be white light by mixing and arranged in positions where the light are emitted to the surface of a solid bounded by curved surface to be inspected obliquely from above at different angles of inclination, light amount adjusting means for adjusting the amount of light of each of the light sources such that the light emitted from the light sources are mixed to be white light, imaging means for imaging reflected light from the surface of the solid bounded by curved surface to be inspected directly over the solid to obtain imaged patterns by hues (for each color), and processing means for detecting the nature of the element of the curved surface of the above solid bounded by curved surface from the imaged patterns obtained by the above imaging means.

The red light, the green light and the blue light from the ring-shaped light sources are directed to the surface of the solid bounded by curved surface to be inspected at different angles of incidence. The substrate inspecting apparatus is constructed such that images formed by the red, green and blue reflected light can be simultaneously detected from the surface of the solid bounded by curved surface by hues. Consequently, the nature of the solid bounded by curved surface can be detected using the pattern of the hue obtained in a short time. In addition, the red light, the green light and the blue light emitted from the light sources are mixed to be white light. Accordingly, peripheral information indispensable in inspection of a soldered state of mounted parts, for example, information on parts on a substrate (the number, the polarity, the color code or the like of the part) and information on substrate patterns (various marks or the like) can be detected. Thus, the soldered state can be automatically inspected.

However, in such a substrate inspecting apparatus, if the surface of a soldered portion has a gentle slope, its reflected light is introduced into imaging means. On the other hand, if the surface of the soldered portion has a steep slope (at an angle of 45° or more with the surface of the substrate), its reflected light is not incident on the imaging means. Consequently, it becomes difficult to inspect the nature of the soldered portion.

SUMMARY OF THE INVENTION

An object of the present invention is to provide a substrate inspecting apparatus capable of inspecting the nature of a soldered portion irrespective of the angle of the steep surface thereof by allowing inspection of the surface of the soldered portion by adding a second imaging unit.

Another object of the present invention is to provide a substrate inspecting method in which the nature of a soldered portion can be inspected irrespective of the angle of the steep surface thereof by inspecting the surface of the soldered portion utilizing secondary illuminating light.

In order to attain the above described objects, the present invention provides a substrate inspecting apparatus for inspecting a part mounted on a substrate for the nature of its soldered portion, which comprises light projecting means including a plurality of ring-shaped light sources for directing light of different hues (different colors) to the part obliquely from above at different angles of incidence, first imaging means including a color camera for imaging reflected light from the surface of the above portion to be inspected by hues (for each color) on the center line of each of the ring-shaped light sources in a position directly over the part, second imaging means including a color or monochrome camera for imaging the reflected light from the surface of the portion to be inspected in a position around the part, and determining and processing means for detecting the nature of the soldered portion by an imaged pattern obtained by each of the first and second imaging mean to determine whether or not soldering is acceptable.

In order to provide a practical and low cost substrate inspecting apparatus, it is desirable that the light projecting means comprises three ring-shaped light sources, and the second imaging means comprises four monochrome cameras for imaging reflected light of light of a particular hue, which cameras are respectively arranged in positions on all sides around the part.

In a case where light of different hues are incident on the part mounted on the substrate from each of the light sources obliquely from above at different angles of incidence, when the surface of the soldered portion has a gentle slope, each of the light of hues is reflected upward. Accordingly, images formed by reflected light of the light of hues are simultaneously and separately detected by the color camera in the first imaging means.

On the other hand, when the surface of the soldered portion has a steep slope, each of the light of hues is reflected sideward. Accordingly, images formed by reflected light of the light of hues are detected by either the color or monochrome cameras in the second imaging means.

In this case, if the second imaging means comprises color cameras, the images formed by the reflected light of the light of hues are simultaneously and separately detected by the color cameras. On the other hand, if the second imaging means comprises monochrome cameras, only the image formed by the reflected light of the light of a particular hue i detected.

Consequently, a soldered portion can be automatically inspected whether the surface thereof has a gentle slope or a steep slope.

The present invention has been made as described above. Accordingly, even if the surface of the soldered portion is steep, reflected light can be imaged by the second imaging means. Consequently, any soldered portion can be automatically inspected irrespective of the angle of the surface thereof.

Furthermore, if the second imaging means comprises monochrome television cameras, some significant effects can be produced. For example, the cost of the setting of the substrate inspecting apparatus is significantly reduced, so that it is easy to put the apparatus into practice.

In an apparatus for inspecting a part mounted on a substrate for the nature of its soldered portion, the substrate inspecting apparatus according to the present invention comprises light projecting means including a ring-shaped light source for directing white light to the part obliquely from above, first imaging means including a monochrome camera for imaging reflected light from the surface of the portion to be inspected on the center line of the ring-shaped light source in a position directly over the part, second imaging means including a monochrome camera for imaging the reflected light from the surface of the portion to be inspected in a position around the side of the part, and determining and processing means for detecting the nature of the soldered portion by an imaged pattern obtained by each of the first and second imaging means to determine whether or not soldering is acceptable.

Furthermore, in order to obtain more detailed information of the soldered portion, the light projecting means comprises a plurality of ring-shaped light sources, each of the light sources is instantaneously operated in time series to illuminate the part at different angles of incidence, and the image obtained in each of the first and second imaging means is accepted in the determining and processing means in response to timing of illumination.

In a case where white light is directed to the mounted part on the substrate from the ring-shaped light sources, when the surface of the soldered portion has a gentle slope, the white light is reflected upward. Accordingly, an image formed by its reflected light is detected by the first imaging means.

On the other hand, when the surface of the soldered portion has a steep slope, the white light is reflected sideward. Accordingly, an image formed by its reflected light is detected by any one of the monochrome cameras in the second imaging means.

In this case, if the light projecting means comprises a plurality of ring-shaped light sources which are instantaneously operated in time series, more detailed information on the angle of the soldered portion is obtained. Consequently, high-precision substrate inspection can be made.

Therefore, according to the present invention, the soldered portion can be automatically inspected whether the surface thereof has a gentle slope or a steep slope.

The present invention has been made as described above. Accordingly, even if the surface of the soldered portion is steep, reflected light can be imaged by the second imaging means. Consequently, any soldered portion can be automatically inspected irrespective of the angle of the surface thereof.

Additionally, according to the present invention, the first and second imaging means comprise monochrome television cameras. Consequently, the cost of the setting of the substrate inspecting apparatus is low, so that it is easy to put the apparatus into practical use.

Furthermore, if the light projecting means comprises a plurality of ring-shaped light sources, detailed information on the angle of the soldered portion is obtained. Consequently, some significant effects can be produced. For example, high-precision substrate inspection can be performed.

According to the present invention, in a substrate inspecting method in which light is directed to a part mounted on a substrate by a ring-shaped light source, reflected light from a soldered portion is imaged, and the nature of the soldered portion is detected by its imaged pattern, fluorescent agents are applied to at least the periphery of the soldered portion of the mounted part on the surface of the substrate, the surface coated with the fluorescent agents is exposed to light from the above ring-shaped light source to excite the fluorescent agents and the soldered portion is exposed to secondary illuminating light produced by the fluorescent agents to image its reflected light.

If the angle of the surface of the soldered portion is small, light from the ring-shaped light source is reflected from the surface having a gentle slope, so that its reflected light is imaged. On the other hand, if the surface of the soldered portion is large, secondary illuminating light which is fluorescence is reflected from the surface having a steep slope, so that its reflected light is imaged. Consequently, the soldered portion having a steep slope can be automatically inspected.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 7 is a diagram showing the relation between the acceptability of a soldered state and patterns;

DESCRIPTION OF THE PREFERRED EMBODIMENTS

Figure 1:
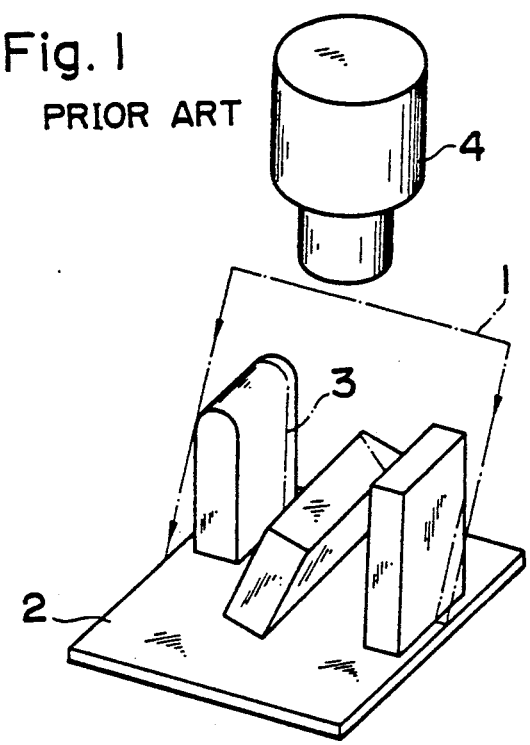
FIG. 1 is a perspective view for explaining the principle of inspection in a conventional automatic inspecting apparatus.
Figure 2:
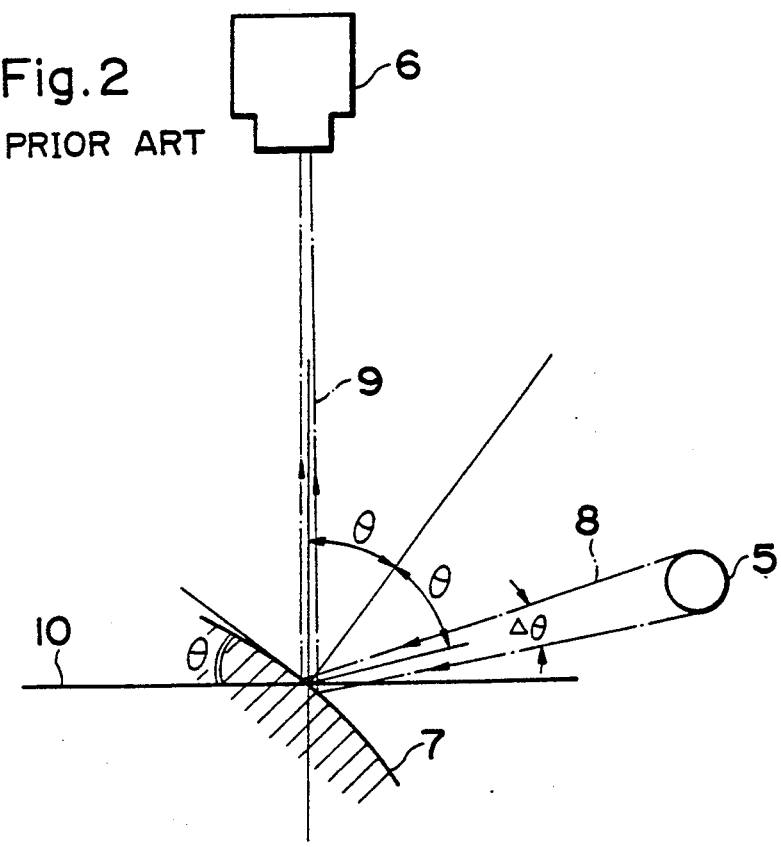
FIGS. 2 and 3 are diagrams for explaining the principle of inspection in the automatic inspecting apparatus.
Figure 3:
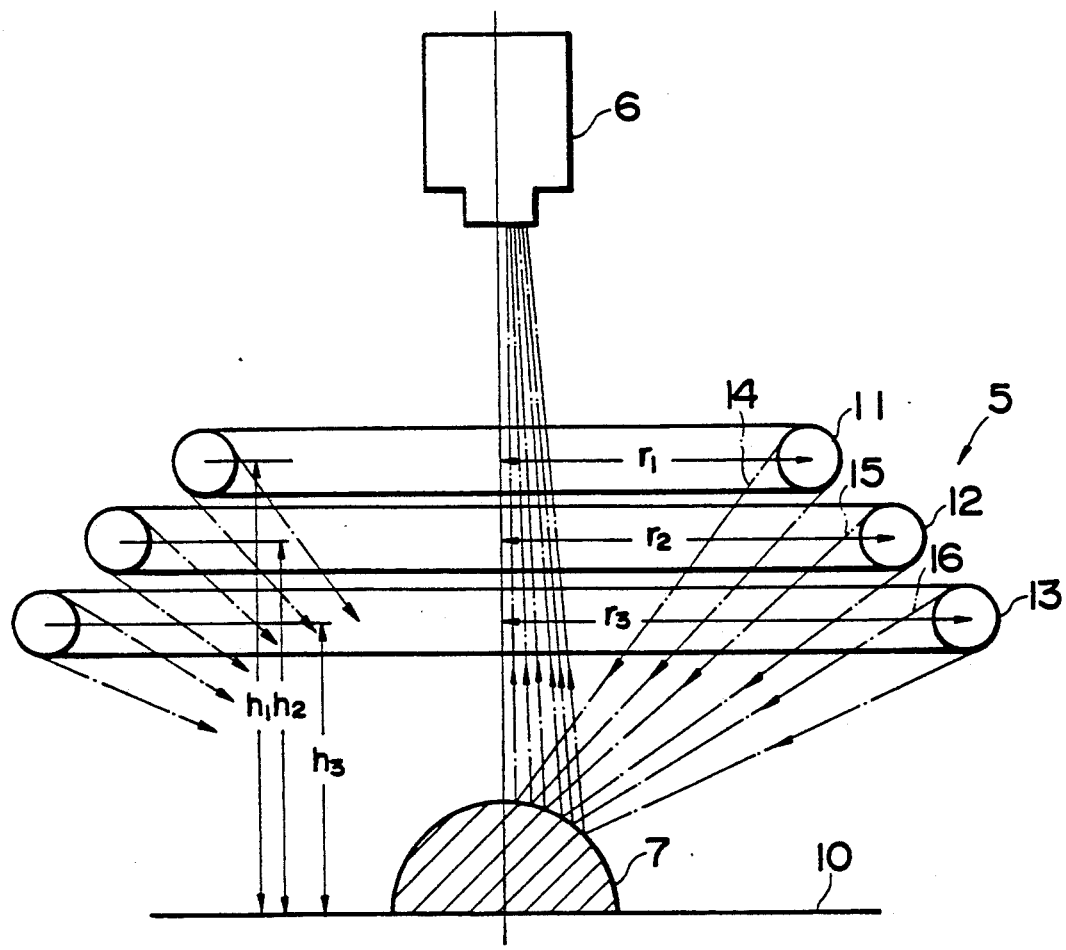
Figure 4:
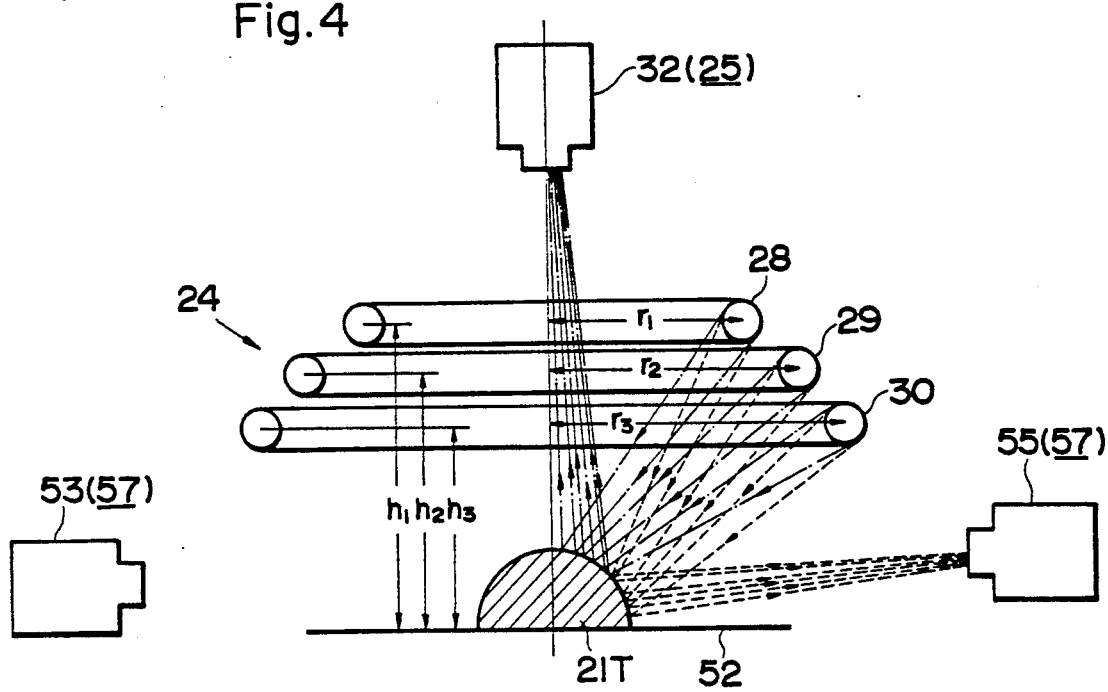
FIG. 4 is a diagram for explaining the principle of a substrate inspecting apparatus according to a first
Figure 5:
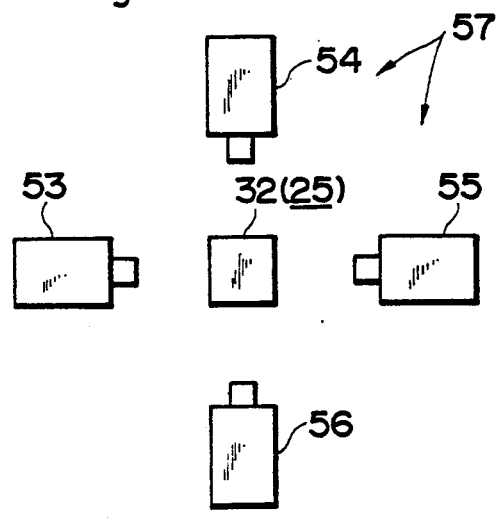
FIG. 5 is a plan view showing the arrangement of cameras in the substrate inspecting apparatus according to the present invention.

FIGS. 4 and 5 show the principle of a substrate inspecting apparatus according to a first embodiment of the present invention, in which a detecting system comprises a light projecting unit 24 including three ring-shaped light sources 28, 29 and 30 having different radii $r_1$, $r_2$ and $r_3$ arranged in positions at different heights $h_1$, $h_2$ and $h_3$ from a reference surface 52, a first imaging unit 25 including a single color television camera 32 located on the center line of each of the ring-shaped light sources and directly over a part 21T to be inspected, and a second imaging unit 57 including a total of four color television cameras 53 to 56 arranged in positions around the part 21T to be inspected for each equal angle of 90°.

The ring-shaped light sources 28, 29 and 30 in the above described light projecting unit 24 direct light of different hues (in this example, red light, green light and blue light) to the part 21T obliquely from above at different angles of incidence. The color television camera 32 in the first imaging unit 25 can detect the element of the curved surface having a gentle slope oriented corresponding to the angle of incidence of a part of light emitted from each of the light sources (represented by dot-and dash line). In addition, the color television cameras 53 to 56 in the second imaging unit 57 can detect the element of the curved surface having a steep slope oriented corresponding to the angle of incidence of another part of light emitted from each of the light sources (represented by a broken line).

Figure 6:
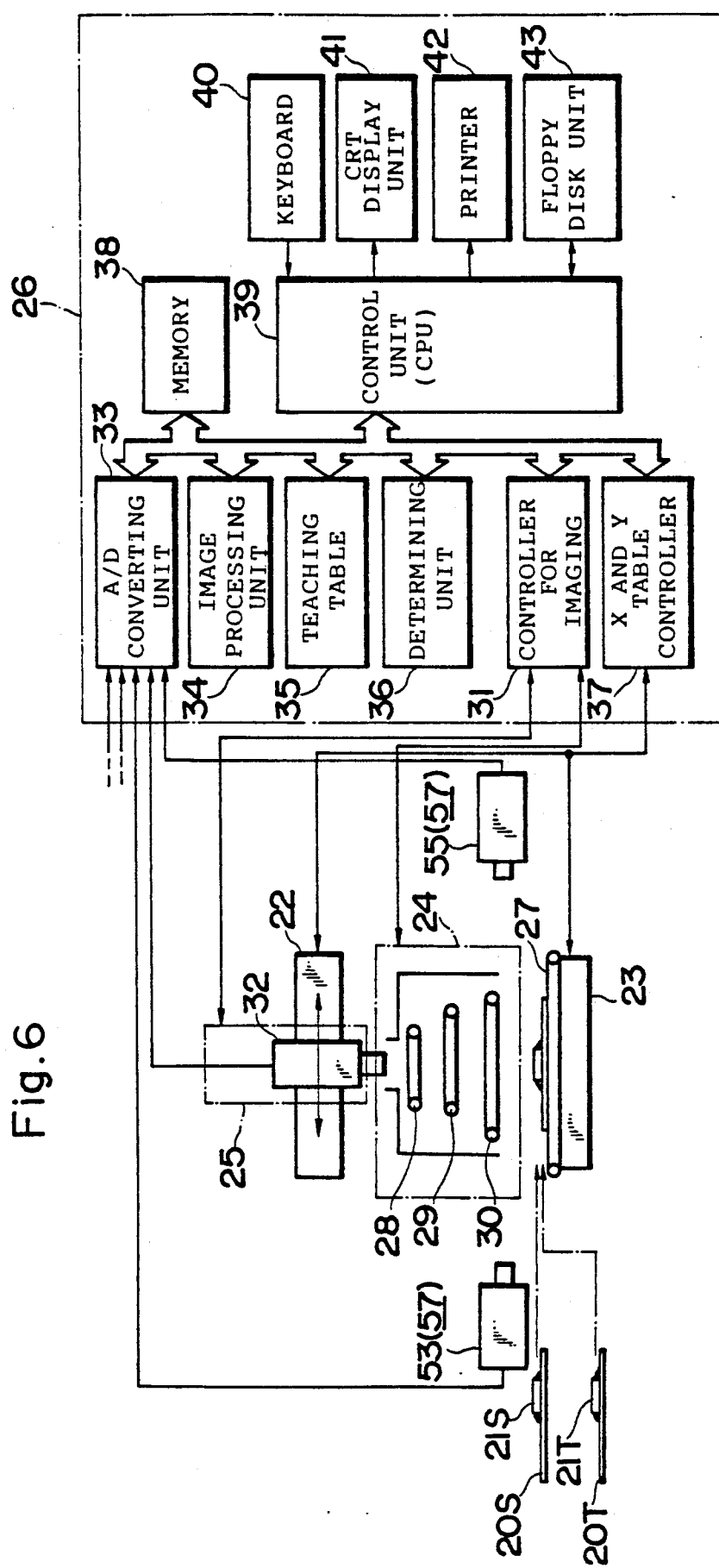
FIG. 6 is a block diagram showing the entire construction of a substrate inspecting apparatus according to a first embodiment of the present invention.

FIG. 6 shows the entire construction of a substrate inspecting apparatus in which the above described detecting system is used.

This substrate inspecting apparatus is used for comparing a feature parameter (determining data) in a region to be inspected of each of parts 21S on a reference substrate (positioning substrate) 20S obtained by imaging the reference substrate and processing its imaged data with a feature parameter (data to be checked) in a region to be inspected of each of parts 21T on a substrate 20T to be inspected obtained by imaging the substrate 20T to be inspected, to make inspection as to whether or not the parts 21T are properly mounted and soldered, which apparatus comprises an X axis table unit 22, a Y axis table unit 23, a light projecting unit 24, a first imaging unit 25, a second imaging unit 57, and a processing unit 26.

The X axis table unit 22 and the Y axis table unit 23 respectively comprise motors (not shown) controlled by a control signal from the processing unit 26. Driving of the motors causes the X axis table unit 22 to move the first imaging unit 25 in the X direction while causing the Y axis table unit 23 to move a conveyor 27 for supporting the substrate 20S or 20T in the Y direction.

The substrates 20S and 20T are illuminated by the light projecting unit 24 and imaged by the first and second imaging units 27 and 57.

The light projecting unit 24 comprises ring-shaped light sources 28, 29 and 30 for respectively producing red light, green light and blue light in response to the control signal from the processing unit 26 to direct the light to an object to be inspected at different angles of incidence. The substrate 20S or 20T is illuminated by light obtained by mixing light of three primary colors emitted from the light sources 28, 29 and 30. An image formed by its reflected light is converted into an electrical signal by the first and second imaging units 25 and 57. In the present embodiment, the light sources 28, 29 and 30 respectively have structures in which a white light source is coated with red, green and blue colored transparent plates (color filters). However, the light sources are not limited to those having such structures provided that they produce light of three primary colors. For example, three ring-shaped (red, green and blue) fluorescent lamps and three ring-shaped (red, green and blue) neon tubings can be also used.

Furthermore, in order to detect information about parts on the substrates 20S and 20T (the number, the polarity, the color code and the like of the part) and information on substrate patterns (various marks and the like) under illumination of the light projecting unit 24, the light sources 28, 29 and 30 are adapted such that light of different hues produced therefrom are mixed to be complete white light. More specifically, the light sources 28, 29 and 30 are adapted to respectively emit such light of the red spectrum, the green spectrum and the blue spectrum, each having a light energy distribution (whose peak is set to 1 (100%)) using the wavelength to enter the horizontal axis, as to be white light by mixing. In addition, the amount of light of different hues outputted from the light sources 28, 29 and 30 is adjusted such that red light, green light and blue light emitted from the light sources 28, 29 and 30 are mixed to be white light by a controller 31 for imaging.

The first imaging unit 25 comprises a color television camera 32 located above the light projecting unit 24. Reflected light from the substrate 20S or 20T is converted into color signals R, G and B of three primary colors by this color television camera 32, to be supplied to the processing unit 26.

Furthermore, the second imaging unit 57 comprises a total of four color television cameras 53, 54, 55 and 56 located on all sides around the substrate 20S or 20T. Light reflected sideward from the above substrate 20S or 20T is converted into color signals R, G and B of three primary colors by the color television camera located in the direction of the reflection, to be supplied to the processing unit 26.

The processing unit 26 comprises an A/D converting unit 33, an image processing unit 34, a teaching table 35, a determining unit 36, a controller 31 for imaging, an X and Y table controller 37, a keyboard 40, a CRT display unit 41, a printer 42, a floppy disk unit 43, a memory 38, and a control unit (CPU) 39. In the teaching mode, the position where each part 21S is to be mounted on the reference substrate 20S, the type of the part to be mounted, the direction of mounting the part and a region to be inspected of the part are detected and the color signals R, G and B associated with the reference substrate 20S are processed. thereby to detect red, green and blue patterns with respect to the region to be inspected of the part 21S in a good soldered state to generate feature parameters. Consequently, a file holding determining data is created. Furthermore, in the inspection mode, the processing unit 26 processes the color signals R, G and B associated with the substrate 20T to be inspected, thereby to detect the patterns of the same colors with respect to a region to be inspected of each part 21T on the substrate 20T to generate feature parameters. Consequently, a file holding data to be inspected is created. The file holding data to be inspected and the above file holding determining data are compared with each other. From the results of this comparison, it is automatically determined whether or not a soldered portion is acceptable with respect to a predetermined part 21T on the substrate 20T to be inspected.

FIG. 7 is a list showing the relation between the cross-sectional shapes of solder 44 in states where soldering is acceptable, any of parts are missing, and solder is insufficient in quantity, and the imaged pattern, the red pattern, the green pattern and the blue pattern imaged by the first imaging unit 25 in the above cases. A distinct difference appears between the color patterns. Consequently, it can be determined whether or not any of parts exist and whether or not soldering is acceptable. The imaged pattern, the red pattern, the green pattern and the blue pattern generated by the second imaging unit 57 are the same as described above (patterns are different from above) and hence, the illustration and the description thereof are not repeated.

Turning to FIG. 6, the A/D converting unit 33 converts the color signals R, G and B into digital signals to apply the same to the control unit 39 when the color signals are supplied from the first and second imaging units 25 and 57. The memory 39 comprises a RAM and is used as a work area of the control unit 39. The image processing unit 34 subjects image data supplied through the control unit 39 to image processing to create the above file holding data to be inspected and the above file holding determining data, to supply the files to the control unit 39 and the determining unit 36.

The teaching table 35 stores the file holding determining data when it is supplied from the control unit 39 in the teaching mode, and reads out the file holding determining data according to a transfer request when the control unit 39 outputs the transfer request in the inspection mode, to supply the file to the control unit 39 and the determining unit 36.

The determining unit 36 compares the file holding determining data supplied from the control unit 39 in the inspection mode with the file holding data to be inspected transferred from the image processing unit 34 to determine whether or not a soldered state is good with respect to the substrate 20T to be inspected, to output the results of the determination to the control unit 39.

The controller 31 for imaging comprises, for example, an interface for connecting the control unit 39, the light projecting unit 24 and the first and second imaging units 25 and 57 and exercises control, for example, adjusts the amount of light from the light sources 28, 29 and 30 in the light projecting unit 24 in response to a command from the control unit 39 and maintains a balance between light outputs of hues of the color television cameras 32 and 53 to 56 in the first and second imaging units 25 and 57.

The X and Y table controller 37 comprises, for example, an interface for connecting the control unit 39, the X axis table unit 22 and the Y axis table unit 23 and controls the X axis table unit 22 and the Y axis table unit 23 in response to an output of the control unit 39.

The CRT display unit 41 comprises a cathode-ray tube (CRT) and displays image data, the results of determination, key input data or the like on its screen when it is supplied from the control unit 39. The printer 42 prints out the results of determination or the like in accordance with a predetermined format when it is supplied from the control unit 39. The keyboard 40 comprises various keys required for entering information on operations, data on the reference substrate 20S and the substrate 20T to be inspected, or the like. The information, the data or the like inputted from this keyboard 40 is supplied to the control unit 39.

The control unit 39 includes a microprocessor and the like and controls operations in teaching and inspection along the following procedure.

Figure 8:
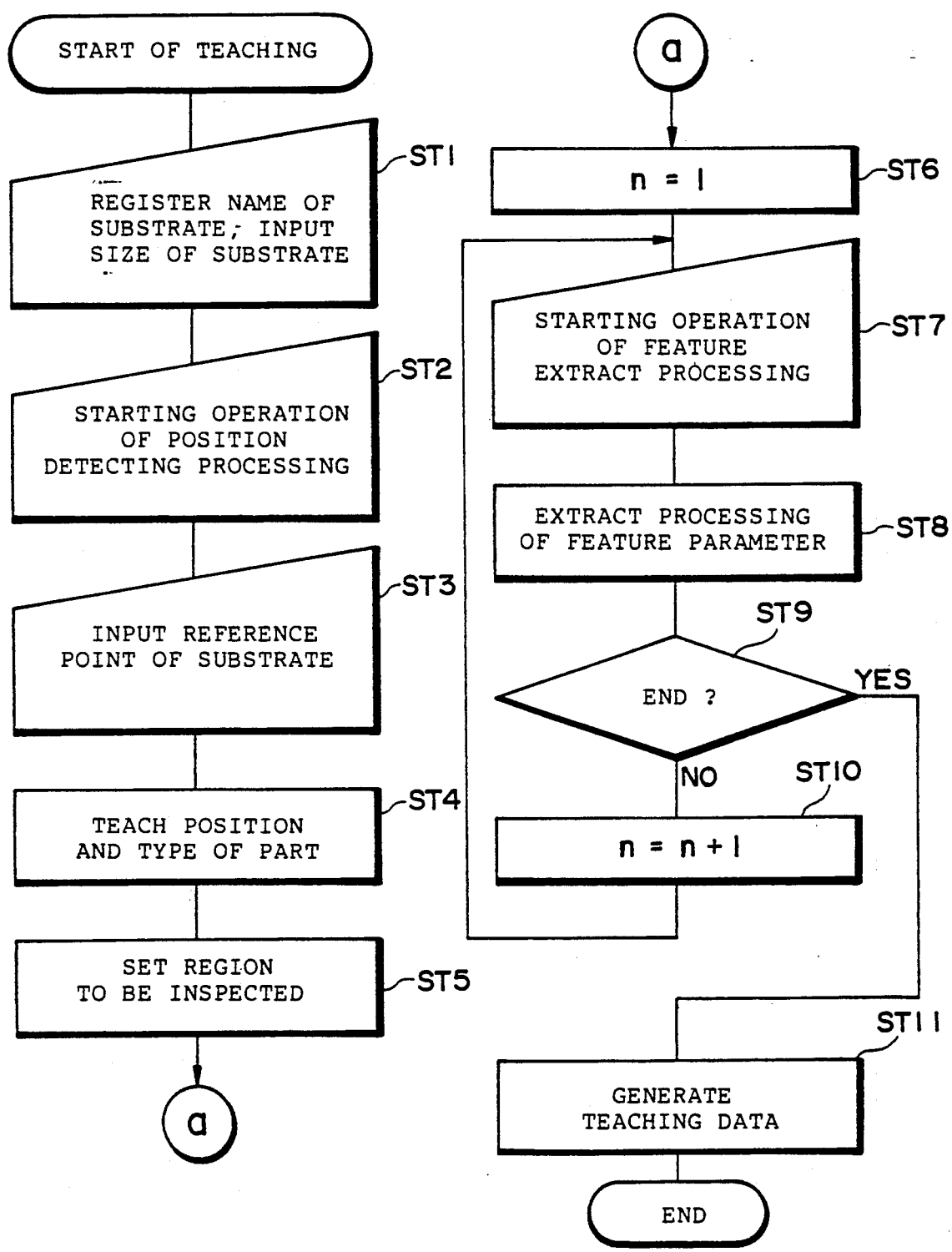
FIG. 8 is a flow chart showing the procedure for teaching processing.

Referring now to FIG. 8, an example of the teaching operation will be described. The control unit 39 turns the light projecting unit 24 and the first and second imaging units 25 and 57 on and arranges the conditions of imaging and the conditions of data processing. In the step (referred to as "ST1" in the drawing), an operator operates the keyboard 40, to register the name of a substrate which is an object to be teached and input the size of the substrate. Thereafter, in the next step 2, the operator sets the reference substrate 20S on the Y axis table unit 23 and depresses a start key. In the step 3, upper right-hand and lower left-hand corner portions are imaged in the first imaging unit 25 as the origin of the reference substrate 20S and displayed on the CRT 41. When the operator positions the cursor in each of the above corner portions and depresses a particular key, the coordinates of the cursor position are inputted as the coordinates of the above corner portion. The control unit 39 controls the X axis table unit 22 and the Y axis table unit 23 on the basis of data on the coordinates inputted, to place the reference substrate 20S in its initial position.

The reference substrate 20S has been in a satisfactorily mounted state by suitably soldering a particular part 21S in a predetermined position where the part is to be mounted. Labels representing the type of the part, the position where the part is to be mounted, and the direction of mounting the part by the shape, the color or the like are affixed on the upper surface of each part 21S. In the step 4, the label of the part 21S is imaged by the first imaging unit 25 and its imaged data is analyzed by the image processing unit 34, thereby to teach the type of the part and the position where the part is mounted.

Subsequently, in the step 5, teaching processing of a region to be inspected is performed. In general, the part comprises a lot of leads around its periphery. The leads are soldered on the substrate. A region around the leads is a region to be inspected. The reference substrate 20S having a predetermined part 21S suitably mounted in its predetermined position is set on the Y axis table unit 23 in the same manner and is imaged by the first imaging unit 25. A region to be inspected is extracted from an image obtained by the imaging. All parts 21S on the reference substrate 20 are subjected to the processing.

When teaching for setting the region to be inspected is completed, the program proceeds to the procedure for teaching a feature parameter.

First, in the step 6, a counter n for counting the number of substrates in the control unit 39 is initialized to one. Then, when in the next step 7, the operator sets the first reference substrate 20S (having a predetermined par suitably mounted and soldered in its predetermined position) on the Y axis table unit 23 and depresses the start key of the keyboard 40, the control unit 39 controls the X axis table unit 22 and the Y axis table unit 23 in response to data on the position of the part and data on the region to be inspected which are obtained by previous teaching, to sequentially position the fields of view of the television cameras 32 and 53 to 56 in parts, to image the reference substrate.

The color signals R, G and B of three primary colors obtained by imaging the substrate using the cameras are converted into digital data in the A/D converting unit 33 and stored in the memory 38 in real time. Then, the control unit 39 extracts land portions within a region to be inspected of each of the parts obtained by the previous teaching, and reads out image data of respective hues concerning the land portions from the memory 38 to transfer the same to the image processing unit 34. In the image processing unit 34, the image data of respective hues are binarized by a suitable threshold value for each hue, for example, to detect a normal soldered state of each of the land portions as red, green and blue patterns and calculate features of the patterns as feature parameters.

When extraction processing of a plurality of feature parameters is completed for each part with respect to the first reference substrate 20S, the substrate is conveyed. Thereafter, the above described counter n is incremented by one (step 10), so that the second reference substrate 20S is designated. Accordingly, extract processing of the feature parameters is repeated through the same procedure as described above.

When the extract processing of the feature parameters is thus terminated with respect to a predetermined number (n) of reference substrates 20S, the determination in the step 9 is in the affirmative. Consequently, the program proceeds to the step 11. In the step 11, the control unit 39 subjects each of the feature parameters associated with the n reference substrates 20S to statistical processing to calculate the average value and the standard deviation so as to obtain the average amount of features for each of the parts, creates a file holding determining data taking the range corresponding to (average value constant x standard deviation) as a normal range to store the file in the teaching table 35, and corrects data as required to terminate teaching.

When teaching is completed in the above described manner, this substrate inspecting apparatus enters a state where the substrate 20T to be inspected after soldering can be automatically inspected.

Figure 9:
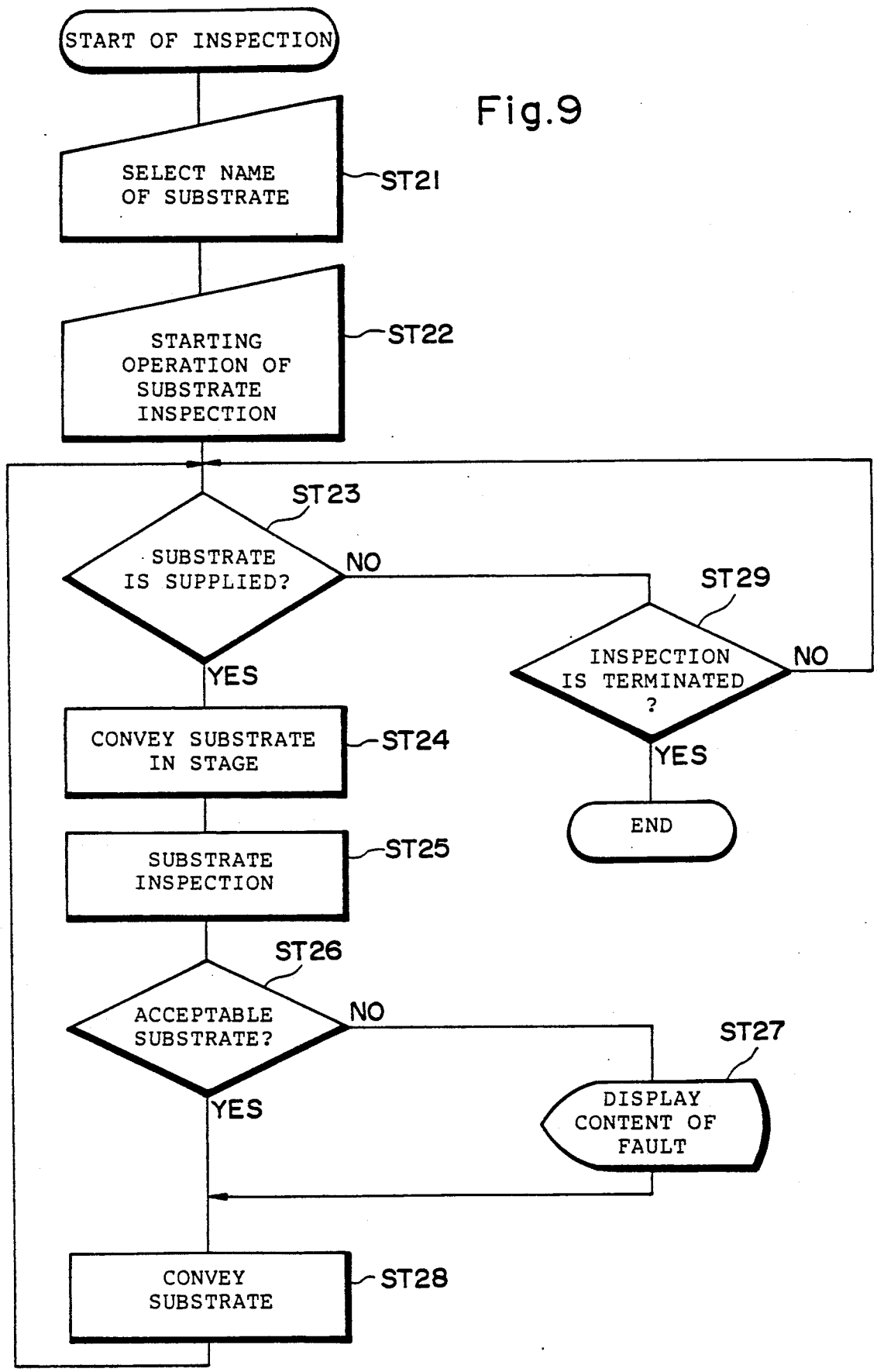
FIG. 9 is a flow chart showing the procedure for inspection processing.

In the inspection mode shown in FIG. 9, the operator selects the name of a substrate to be inspected to perform a starting operation of substrate inspection, in the steps 21 and 22.

In the next step 23, the supply of the substrate 20T to be inspected to the substrate inspecting apparatus is checked. If the substrate 20T to be inspected is supplied, a conveyor 27 is operated. Accordingly, the substrate 20T to be inspected is conveyed into the Y axis table unit 23, to start substrate inspection (steps 24 and 25).

In the step 25, the control unit 39 controls the X axis table unit 22 and the Y axis table unit 23, positions the fields of view of the television cameras 32 and 53 to 56 with respect to the first part 21T on the substrate 20T to be inspected to image the substrate, automatically extracts land portions in the region to be inspected, and calculates feature parameters in each the land portions, to create a file holding data to be inspected. Thereafter, the control unit 39 transfers the above file holding data to be inspected to the determining unit 36. The determining unit 36 compares this file holding data to be inspected with the above file holding determining data, to determine whether or not soldering is acceptable with respect to the first part 21T.

Such inspection is repeatedly made with respect to all the parts 21T on the substrate 20T to be inspected. As a result, if soldering is not acceptable, the faulty part and the contents of the fault are displayed on the CRT display unit 41 or printed by the printer 42. Thereafter, the substrate 20T to be inspected is conveyed from a position where inspection is made (steps 27 and 28).

Thus, when the same procedure for inspection is performed with respect to all the substrates 20T to be inspected, the determination in the step 29 is "YES", so that substrate inspection is completed.

Figure 10:
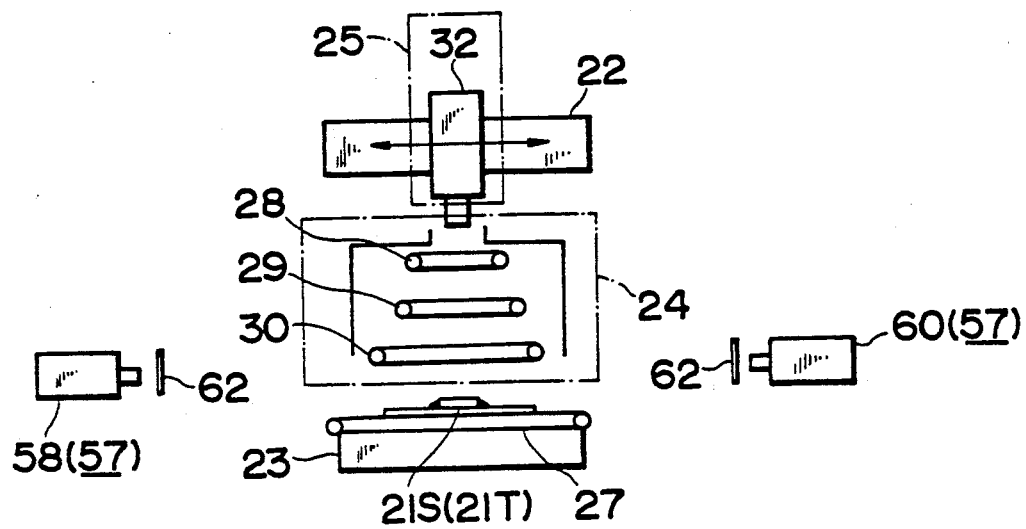
FIGS. 10 and 12 are diagrams showing modified examples of the first embodiment.

FIG. 10 shows a first modified example of the detecting system in the substrate inspecting apparatus In the embodiment shown in FIG. 10, as the second imaging unit 57, the above described color television cameras 53 to 56 are replaced with monochrome television cameras 58 to 61 (cameras 59 and 61 are not shown). Each of the monochrome television cameras 58 to 61 is used for imaging only reflected light of light of a particular hue (for example, blue light) and comprises a band-pass filter 62 for passing only the light of the hue in a position, on which light is incident, of the camera.

In this first modified example, the second imaging unit 57 comprises four monochrome television cameras 58 to 61. Consequently, the cost of the setting of the substrate inspecting apparatus can be significantly reduced, so that it is easier to put the apparatus into practice, as compared with the first embodiment previously described in detail. In addition, the number of imaged patterns obtained by the second imaging unit 57 is decreased. Accordingly, the speed of image processing can be increased and the memory capacity can be decreased.

Figure 11:
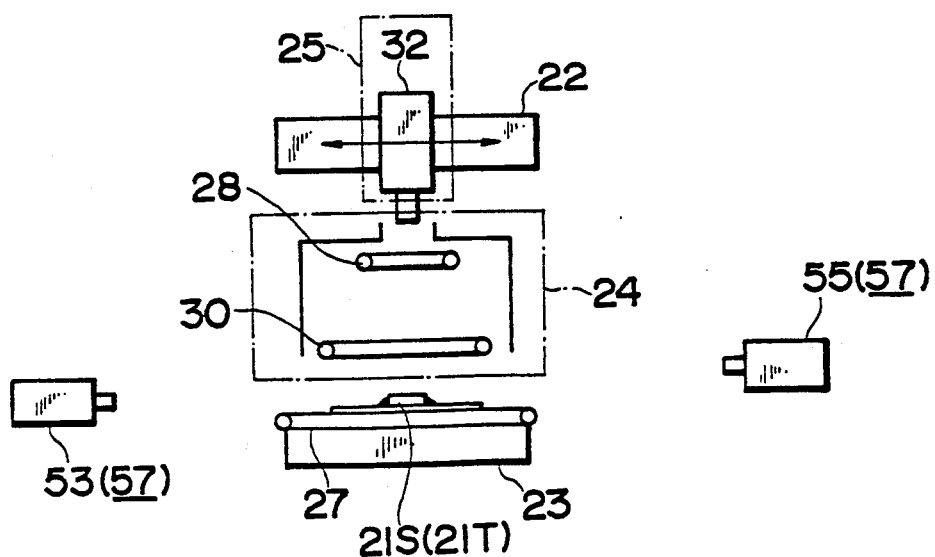

FIG. 11 shows a second modified example of the detecting system.

In the modified example shown in FIG. 11, the color television cameras 53 to 56 are used as the second imaging unit 57 but any one of the light sources constituting the light projecting unit 24 (in this example, the ring-shaped light source 29 emitting green light) is omitted and only the two ring-shaped light sources 28 and 30 are used.

In this second modified example, the number of imaged patterns obtained by the first and second imaging units 25 and 57 is decreased, as compared with the first embodiment. Accordingly, the speed of image processing can be increased and the memory capacity can be decreased. Similarly, the cost of the setting of the substrate inspecting apparatus can be reduced.

Figure 12:
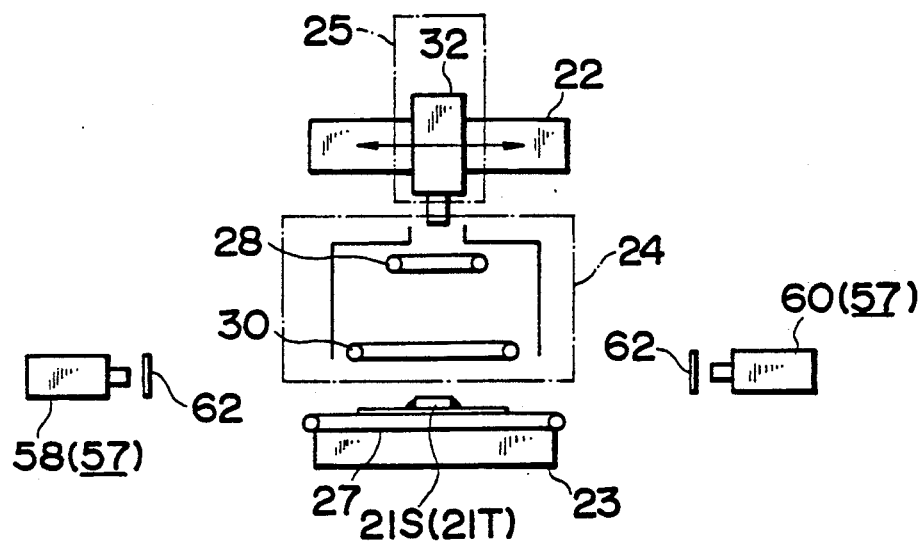

FIG. 12 shows a third modified example of the detecting system.

In the embodiment shown in FIG. 12, the monochrome television cameras 58 to 61 and the band-pass filter 62 are used as the second imaging unit 57, and any one of the light sources constituting the light projecting unit 24 (in this example, the ring-shaped light source 29 emitting green light) is omitted and only the two ring-shaped light sources 28 and 30 are used.

In this third modified example, the second imaging unit 57 comprises four monochrome television cameras 58 to 61. Accordingly, the cost of the setting of the substrate inspecting apparatus can be significantly reduced, as compared with the first embodiment. In addition, the number of imaged patterns obtained by the first and second imaging units 25 and 57 is decreased. Accordingly, the speed of image processing can be increased and the memory capacity can be decreased. Consequently, the cost of the setting of the apparatus can be further reduced.

Meanwhile, in the above described first to third modified examples, the construction of the processing unit 26 and the procedures for teaching and inspection are the same as those in the first embodiment.

Figure 13:
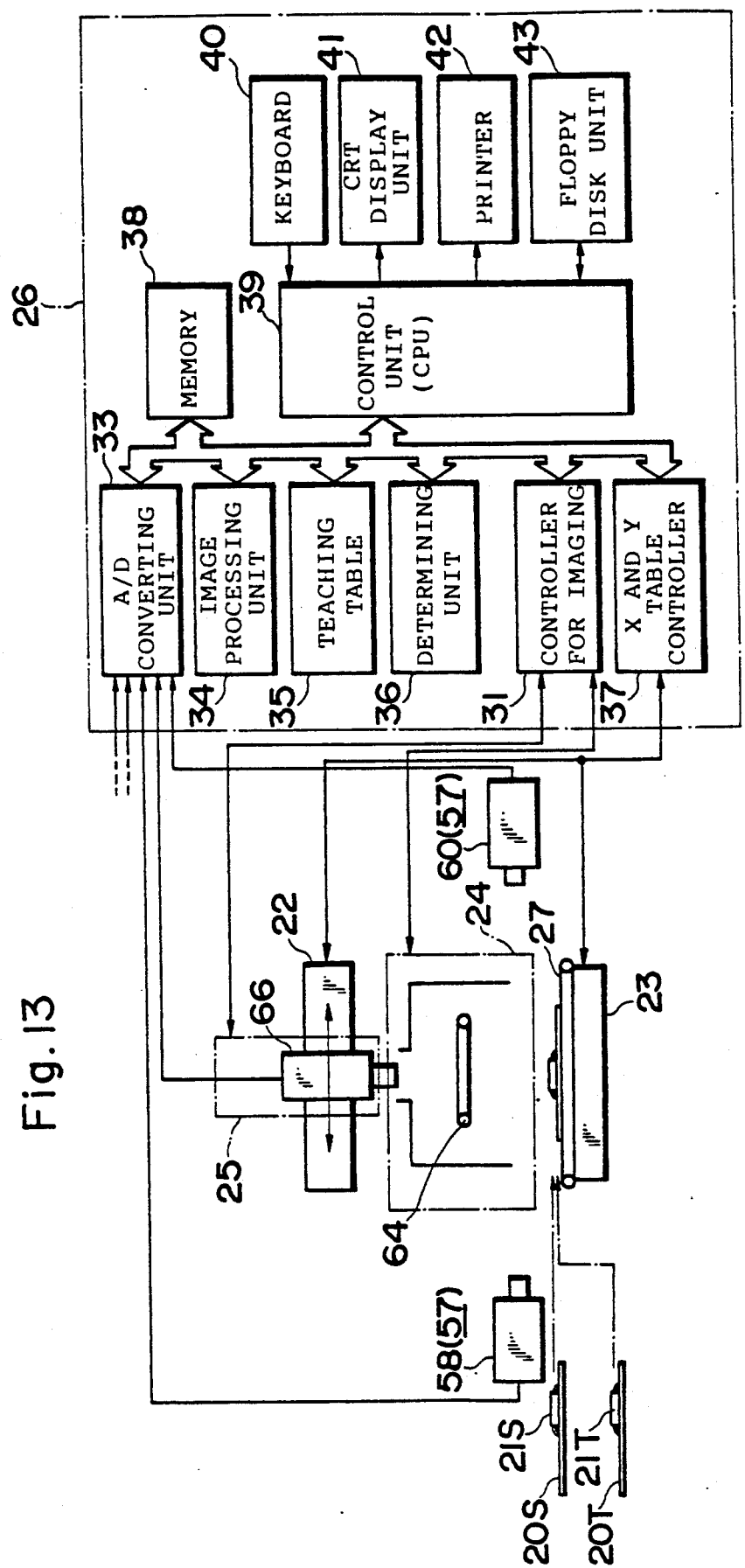
FIG. 13 is a block diagram showing the entire construction of a substrate inspecting apparatus according to a second embodiment of the present invention.

FIG. 13 illustrates a substrate inspecting apparatus according to a second embodiment of the present invention. The same reference numerals are assigned to the same portions and hence, the description thereof is not repeated.

A light projecting unit 24 comprises a ring-shaped light source 64 for producing white light in response to a control signal from a processing unit 26 and directing the light to an object to be inspected at a predetermined angle of incidence. The white light emitted from this light source 64 is projected onto the above described substrates 20S and 20T, to obtain images formed by its reflected light in the first and second imaging units 25 and 57 and convert the images into electrical signals.

Then, the first imaging unit 25 comprises a monochrome television camera 66 located on the center line of the light source 64 above the light projecting unit 24. Light reflected upward from the above described substrate 20S or 20T is converted into a video signal by this monochrome television camera 66, to be supplied to the processing unit 26.

Furthermore, the second imaging unit 57 comprises a total of four monochrome television cameras 58, 59, 60 and 61 (only the cameras 58 and 60 are shown) located on all sides around the substrate 20S or 20T at intervals of an angle of 90°. Light reflected sideward from the described substrate 20S or 20T is converted into a video signal by the monochrome television camera located in the direction of the reflection, to be supplied to the processing unit 26.

In the monochrome television camera 66 in the first imaging unit 25, the element constituting the curved surface having a gentle slope oriented corresponding to the angle of incidence of a light beam from the light source 68 can be detected. On the other hand, in the monochrome television cameras 58 to 61 in the second imaging unit 57, the element of the curved surface having a steep slope oriented corresponding to the angle of incidence of a light beam from the light source 64 can be detected.

Also in this second embodiment, teaching processing shown in FIG. 8 and inspection processing shown in FIG. 9 can be applied without any modification. In the second embodiment, however, the light projecting unit 24 projects white light and both the first and second imaging units 25 and 57 comprise monochrome television cameras. Consequently, red, green and blue patterns shown in FIG. 7 can not be detected, so that inspection is performed according to only a monochrome imaged pattern.

Figure 14:
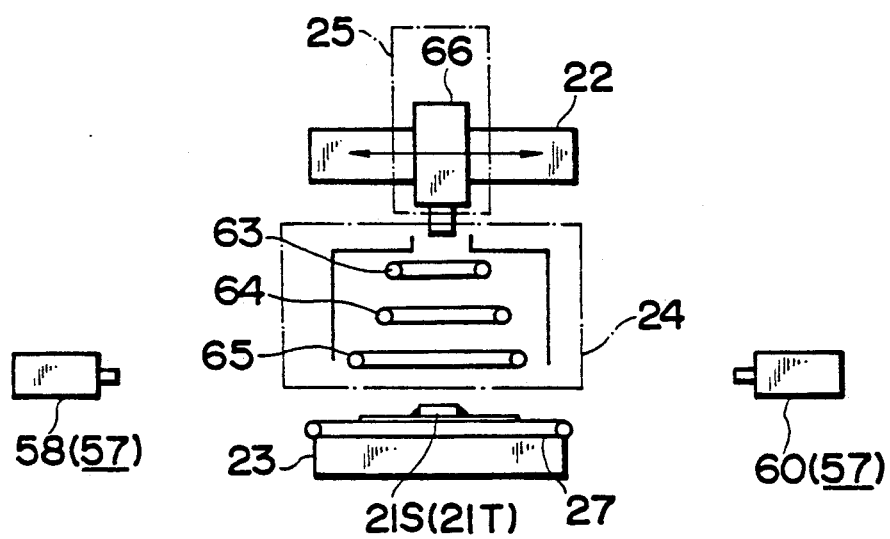
FIG. 14 is a diagram showing a modified example of the second embodiment.

FIG. 14 shows a modified example of the detecting system in the substrate inspecting apparatus according to the second embodiment.

In the modified example shown in FIG. 14, the light projecting unit 24 comprises three ring-shaped light sources 63, 64 and 65 having different radii horizontally arranged in positions at different heights with their center lines coinciding with each other and causes the light sources 63, 64 and 65 to perform an instantaneous operation (stroboscopic light emitting operation) in time series, to direct white light to parts 21S and 21T at different angles of incidence. As a result, the first and second imaging units 25 and 57 form images of the parts 21S and 21T in response to timing of directing light by the light sources. Accordingly, the images are sequentially accepted in the processing unit 26, to be processed.

In this modified example, more detailed information on the angle of a soldered portion can be obtained, as compared with the second embodiment. Consequently, high-precision substrate inspection can be performed.

Figure 15:
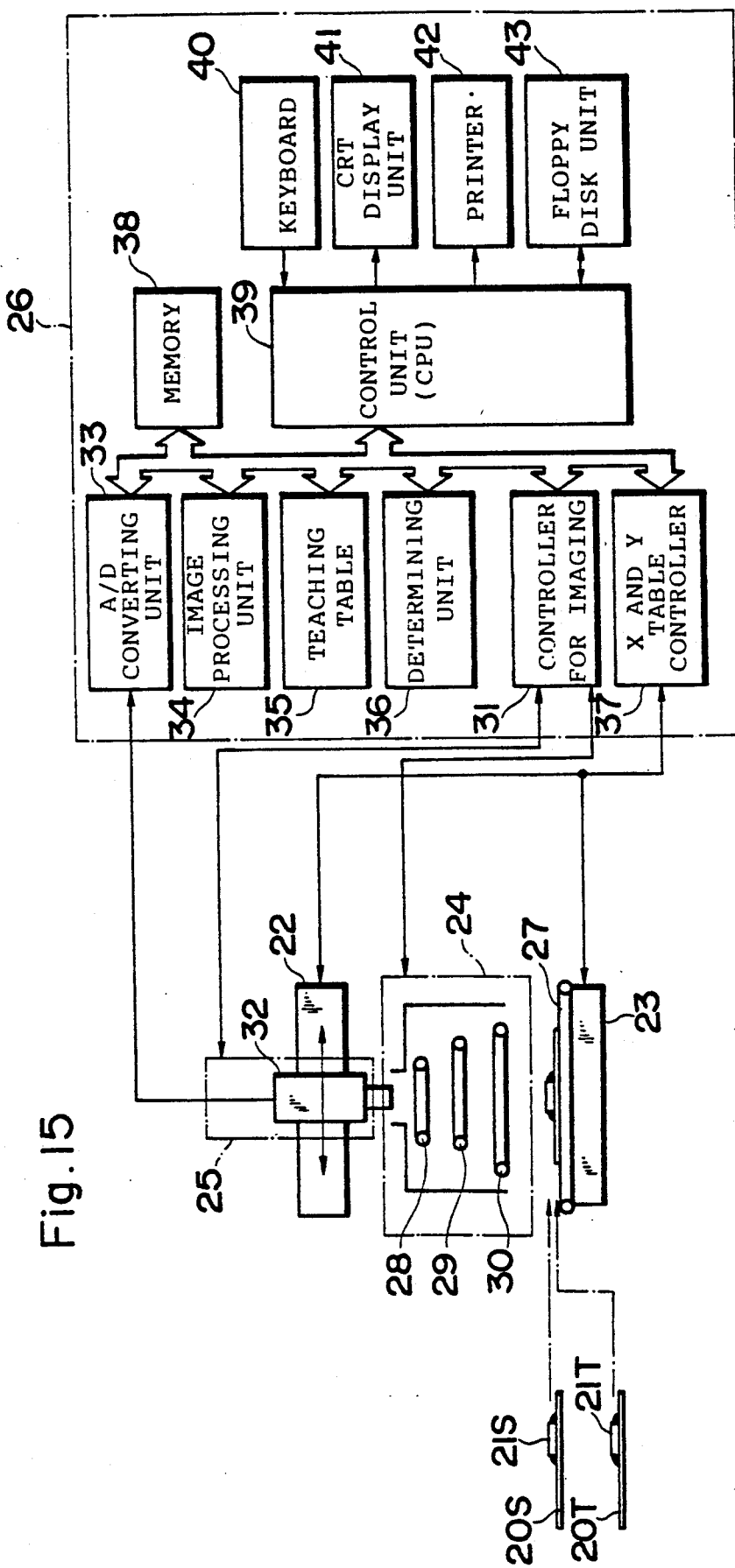
FIG. 15 is a block diagram showing the entire structure of a substrate inspecting apparatus according to a third embodiment of the present invention.

FIG. 15 shows a substrate inspecting apparatus according to a third embodiment of the present invention. The same reference numerals are assigned to the same portions as those shown in FIG. 6. The substrate inspecting apparatus shown in FIG. 15 is the same as that shown in FIG. 6 except that no second imaging unit is provided.

Figure 16:
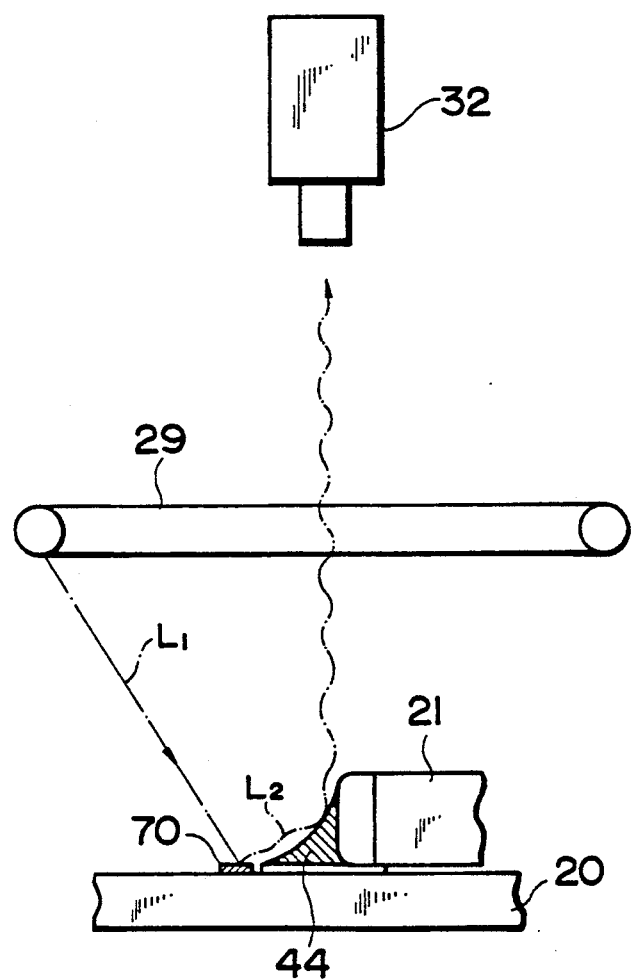
FIG. 16 is a diagram showing the principle of a substrate inspecting method according to the third embodiment.

FIG. 16 shows the principle of a substrate inspecting method using the apparatus according to the third embodiment.

This substrate inspecting method is a method of directing light to a mounted part 21 (21S or 21T) on a substrate 20 (20S or 20T) from a ring-shaped light source 29 (shown as a representative of light sources 28 to 30), photographing an image formed by reflected light from the surface of a soldered portion 44 by a television camera 32 in an imaging unit 25, and detecting the nature of the soldered portion 44 by its imaged pattern. Fluorescent agents 70 are applied to at least the periphery of the soldered portion 44 of the mounted part 21. When a surface coated with the fluorescent agents (70) is exposed to light $L_1$ from the ring-shaped light source 29, fluorescence $L_2$ is emitted.

In a portion where the angle of the surface of the soldered portion 44 with the substrate 20 is small, the light $L_1$ from the light source 29 is reflected from the gentle slope, so that an image formed by the reflected light is directly photographed by the television camera 32. On the other hand, in a portion where the angle of the surface of the soldered portion 44 with the substrate 20 is large, the fluorescence $L_2$ serving as secondary illuminating light is reflected from the steep slope, so that an image formed by the reflected light is imaged by the television camera 32. Accordingly, the nature of the soldered portion can be determined irrespective of that the soldered portion has a large angle or the soldered portion includes a portion having a large angle. Consequently, the soldered portion can be automatically inspected.

Figure 17:
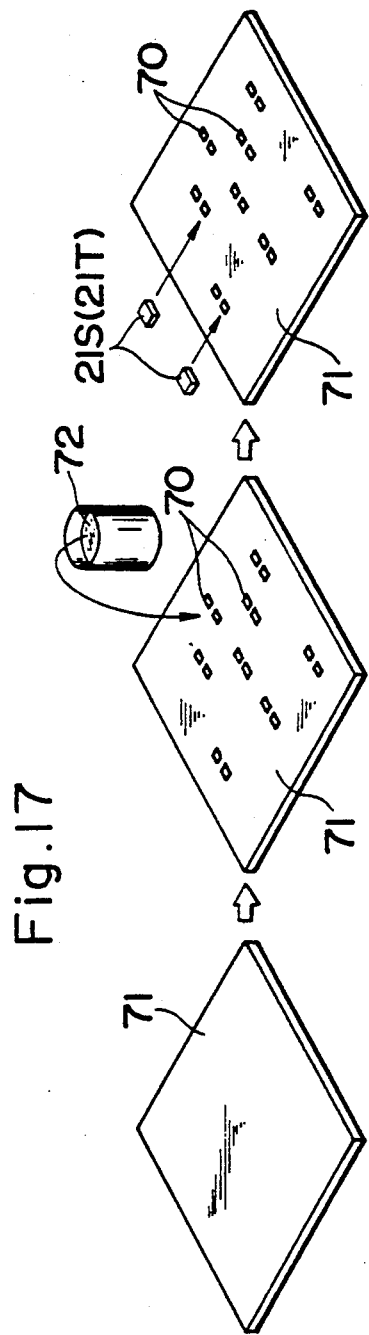
FIG. 17 is a perspective view showing the steps of fabricating a substrate.

The above described reference substrate 20S and substrate 20T to be inspected are formed as shown in FIG. 17. First, an unprocessed substrate whose both surfaces (or one surface) are coated with copper thin film is subjected to etching processing, resist processing, punching processing or the like (a hole provided by the processing is not shown), to form a semi-processed substrate 71. Then, coatings or ink 72 including fluorescent agents are applied to positions where parts are to be mounted on the semi-processed substrate 71 by silk screen printing, resist painting, dot marking or the like to form a surface 70 coated with the fluorescent agents and then, predetermined parts 21S and 21T are mounted in the position where parts are to be mounted on the substrate, to form the reference substrate 20S and the substrate 20T to be inspected.

Meanwhile, the above fluorescent agents can be suitably selected. Red fluorescence is obtained using green light and blue light if red fluorescent agents are selected, while green fluorescence is excited using blue light if green fluorescent agents are selected.

Figure 19:
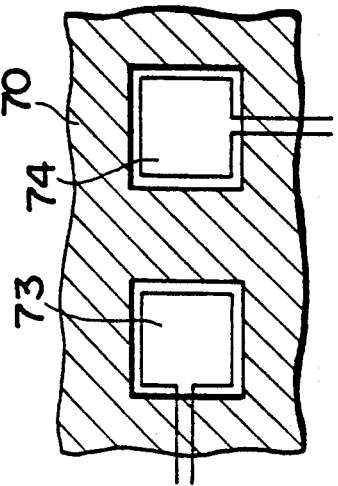
FIGS. 18 and 19 are plan views showing the surface coated with fluorescent agents.
Figure 18:
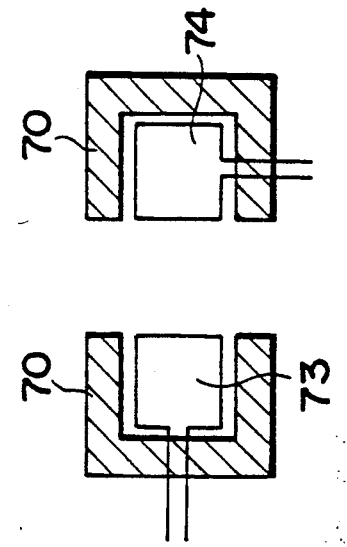

Although in the present embodiment, the above described surface 70 coated with the fluorescent agents is partially formed so as to surround land portions 73 and 74 on which parts are mounted as shown in FIG. 18, the present invention is not limited to the same. For example, the surface 70 may be formed on the entire surface of the substrate excluding the land portions 73 and 74, as shown in FIG. 19.

Operations in the substrate inspecting apparatus according to the third embodiment, that is, teaching shown in FIGS. 8 and 9. The imaging unit 25 includes the color television camera 32. Accordingly, the red pattern, the green pattern and the blue pattern can be obtained in addition to the imaged pattern. In the present embodiment, the inspecting region is complementarily illuminated using secondary illuminating light (having a color peculiar to fluorescent agents) produced from the fluorescent agents. Consequently, the color patterns slightly differ from those shown in FIG. 7. However, substrate inspection can be performed by the same method as that in the first embodiment (provided image data obtained by the second imaging unit is not used).

Figure 20:
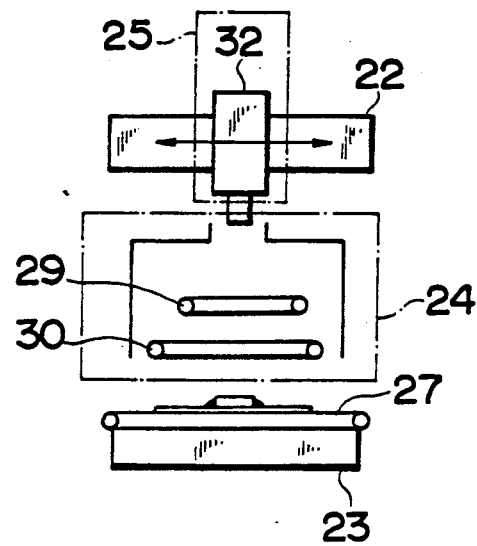
FIGS. 20 and 21 are diagrams showing modified examples of the third embodiment.

FIG. 20 shows a modified example of the third embodiment, in which two light sources, that is, a light source 29 for producing blue light and a light source 30 for producing green light are used as the light projecting unit 24. In this case, red fluorescent agents excited by the green light or the blue light are used as fluorescent agents applied to substrates 20S and 20T. If a light source for producing red light and a light source for producing blue light are used as the light projecting unit 24, however, green fluorescent agents excited by the blue light are used.

Figure 21:
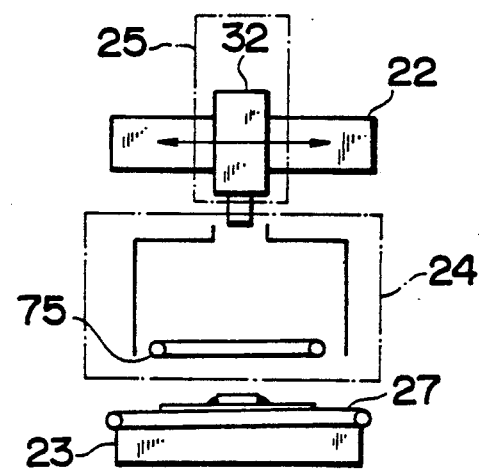

FIG. 21 shows another modified example of the third embodiment, in which a single light source 75 is used as the light projecting unit 24. In this case, red fluorescent agents and green fluorescent agents are used as fluorescent agents applied to substrates 20S and 20T if light emitted from the light source 75 is white light, red fluorescent agents are used if it is green light, and green fluorescent agents are used if it is blue light. Red fluorescence is produced if the red fluorescent agents are exposed to the white light, while green fluorescence is produced if the green fluorescent agents are exposed to the white light.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A substrate inspecting apparatus for inspecting a part mounted on a substrate for the integrity of a soldered portion thereon, comprising:
   light projecting means including a plurality of ring-shaped light sources for directing light of different hues to said part obliquely from one direction at different angles of incidence;
   first imaging means including a color camera for imaging reflected light from the surface of a portion to be inspected by hues on the center line of each of the ring-shaped light sources in a position directly over the part;
   second imaging means including a color or monochrome camera for imaging the reflected light from the surface of said portion to be inspected in a position around the side of the part; and
   determining and processing means for detecting the nature of the soldered portion by an imaged pattern obtained by each of the first and second imaging means to determine whether or not soldering is acceptable.

2. The apparatus according to claim 1, wherein said light projecting means comprises two or three ring-shaped light sources.

3. The apparatus according to claim 1, wherein:
   said light projecting means comprises a plurality of ring-shaped light sources for instantaneously illuminating said part by white light in time series at different angles of incidence, and
   said determining and processing means accepts the image obtained by each of the first and second imaging means in response to timing of instantaneous illumination from each of said light sources and detect the integrity of the soldered portion by a imaged pattern to determine whether or not soldering is acceptable.

4. The apparatus according to claim 1, wherein said second imaging means comprises four color or monochrome television cameras.

5. The apparatus of claim 4, wherein said color or monochrome television cameras are at 90° intervals around the part to be inspected.

6. The apparatus of claim 1, wherein said determining and processing means comprises A/D converting means, image processing means, a teaching table, a determining means, a controller for imaging, and an X and Y table controller.

7. The apparatus of claim 6, further comprising a keyboard.

8. The apparatus of claim 6, further comprising display means.

9. The apparatus of claim 6, further comprising a printer.

10. The apparatus of claim 6, further comprising a memory.

11. The apparatus of claim 6, further comprising a control unit.

12. A substrate inspecting apparatus for inspecting a part mounted on a substrate for the integrity of a soldered portion thereon, comprising:
   light projecting means including a ring-shaped light source for directing white light to said part obliquely from one direction;
   first imaging means including a color camera for imaging reflected light from the surface of a portion to be inspected on the center line of the ring-shaped light source in a position directly over the part;
   second imaging means including a monochrome camera for imaging the reflected light from the surface of said portion to be inspected in a position around the side of the part; and
   determining and processing means for detecting the integrity of the soldered portion by an imaged pattern obtained by each of the first and second imaging means to determine whether or not soldering is acceptable.

13. The apparatus of claim 12, wherein said determining and processing means comprises A/D converting means, image processing means, a teaching table, a determining means, a controller for imaging, and an X and Y table controller.

14. The apparatus of claim 13, further comprising a keyboard.

15. The apparatus of claim 13, further comprising display means.

16. The apparatus of claim 13, further comprising a printer.

17. The apparatus of claim 13, further comprising a memory.

18. The apparatus of claim 13, further comprising a control unit.

19. A substrate inspecting method in which light is directed to a part mounted on substrate from a ring-shaped light source, reflected light from the surface of a soldered portion is imaged and the integrity of the soldered portion is inspected by its imaged pattern, characterized by applying fluorescent agents to at least the periphery of the soldered portion of the mounted part on the surface of said substrate, exposing the surface coated with the fluorescent agents to light from said ring-shaped light source to excite the fluorescent agents, exposing the surface of the soldered portion to secondary illuminating light produced by the fluorescent agents to image light reflected therefrom.

* * * * *